United States Patent [19]
Schildgen et al.

[11] Patent Number: 5,904,669
[45] Date of Patent: May 18, 1999

[54] MAGNETIC BALL VALVE AND CONTROL MODULE

[75] Inventors: Robert M. Schildgen, Gurnee, Ill.; James P. Anderson, Kenosha, Wis.

[73] Assignee: FibraSonics Inc., Chicago, Ill.

[21] Appl. No.: 08/736,968

[22] Filed: Oct. 25, 1996

Related U.S. Application Data

[60] Provisional application No. 60/005,922, Oct. 27, 1995.

[51] Int. Cl.⁶ ................................................ A61M 5/00
[52] U.S. Cl. ............................... 604/246; 604/30; 604/65
[58] Field of Search ................................ 604/30, 31, 33, 604/34, 35, 65, 67, 249, 246

[56] References Cited

U.S. PATENT DOCUMENTS

| | | | |
|---|---|---|---|
| 3,990,452 | 11/1976 | Murry et al. | 128/305 |
| 4,180,074 | 12/1979 | Murry et al. | 128/276 |
| 4,184,510 | 1/1980 | Murry et al. | 137/565 |
| 4,189,286 | 2/1980 | Murry et al. | 417/477 |
| 4,689,040 | 8/1987 | Thompson | 604/22 |
| 5,676,650 | 10/1997 | Grieshaber et al. | 604/31 |
| 5,693,013 | 12/1997 | Geuder | 604/35 |

*Primary Examiner*—Michael Buiz
*Assistant Examiner*—Daphna Shai
*Attorney, Agent, or Firm*—Welsh & Katz, Ltd.

[57] ABSTRACT

An improved valve utilizes a ball or sphere positioned within a housing which is movable by source of magnetic force external to the housing, the housing having a fluid inlet and a fluid outlet, and a sealing member positioned within the housing adjacent the fluid inlet or the fluid outlet. A modular control valve apparatus is provided having at least one or a plurality of valves in the housing, each having a fluid inlet and a fluid outlet, and a passage from a source of fluid or aspiration to an instrument or other device to direct and/or utilize the fluid or aspiration. Control is provided by including one or more pressure monitors, such as diaphragms positioned in recesses in a surface of the housing, coupled to passageways connected to passageways leading to fluid flow conduits. Variations in pressure in the conduits are transmitted from the diaphragm to a sensor such as a transducer to generate a signal, which activates a correcting electronic circuit which in turn controls a pump for a vacuum system. Provision is made to prevent contamination of the monitoring system by providing a hydrophobic filter between each passageway leading to the conduit and the diaphragm.

20 Claims, 4 Drawing Sheets

MAGNETIC BALL VALVE AND CONTROL MODULE

This is a non provisional application, from provisional application Ser. No. 60/005,922, filed Oct. 27, 1995.

BACKGROUND OF THE INVENTION

1. Field of the Invention

This invention relates to valves, particularly valves useful in medical apparatus, and control modules employing valves for controlling medical apparatus during procedures, and, more particularly, to ball valves and control modules employing such valves which are especially useful for controlling surgical procedures requiring irrigation, aspiration and/or control of the pressure within an organ of the body during surgery.

2. Description of Related Art

As noted in U.S. Pat. No. 4,180,074, and related U.S. Pat. No. 4,184,510, the requirements of ultrasonic equipment in surgery, particularly, for example, in surgical procedures requiring aspiration and irrigation, are quite complex and necessitate the precise control of the equipment during these steps. While the two noted patents provide a careful study of the problems encountered and requirements of such control systems, define terms, which definitions are incorporated and used herein, trace the history of such surgeries and equipment which had been used in the past, and provide improved devices and methods for controlling ultrasonic equipment during such procedures; there still exists a need for even more precise control of the equipment during such steps as aspiration and irrigation, particularly during surgical operations as, for example, phacoemulsification and other ophthalmological procedures.

In addition, the use of pinch valves with ultrasonic equipment, as is common, with a switch, usually a foot switch, controlled by the surgeon, often results in an unintended opposite flow of fluid upon the surgeon releasing the switch, with potentially serious results. For example, if the surgical site, such as an eye, is being irrigated with a positive flow of irrigating liquid in or near the eye, a sudden ceasing of the flow may inadvertently cause a negative pressure in the irrigation conduit, and at the tip of the operating end or needle of the handpiece, particularly where the tip is positioned through an incision in the eye, and hence in interocular pressure, resulting in aspiration of fluid including, possibly, aqueous humor. Therefore, there is a need for a device which will provide zero pressure to flow conduits upon the surgeon releasing the switch controlling fluid flow, such as irrigating fluid or aspiration.

SUMMARY OF THE INVENTION

Thus, it is one object of the present invention to provide a new and improved valve which is useful for precisely controlling the flow of a fluid, such as required in irrigation and aspiration during surgical procedures.

Another object of the present invention is to provide a module having an improved valve which is useful for precisely controlling the flow of a fluid.

It is still another object of the present invention to provide a module having a plurality of improved valves whereby the flow or aspiration of several fluid streams, including aspiration, can be precisely controlled concurrently or consecutively without moving or reconnecting fluid flow conduits to a control valve.

Still another object of the present invention to provide a device which provides zero or balanced pressure to flow conduits upon the surgeon releasing a switch controlling fluid flow, such as irrigating fluid or aspiration in surgical equipment.

These and other objects and advantages of the present invention will be apparent from the following description and drawing.

In accordance with the present invention, an improved valve is provided which utilizes a ball or sphere movable by magnetic force, the ball or sphere being positioned within a housing permitting magnetic force to pass therethrough, the housing having a fluid inlet and a fluid outlet, a sealing member positioned within the housing adjacent the fluid inlet or the fluid outlet so as to normally permit fluid to flow between the fluid inlet and the fluid outlet, and a source of magnetic force causing the ball or sphere to be moved between a position in sealing relationship with the sealing member preventing the flow of fluid between the fluid inlet and the fluid outlet and a position other than in sealing relationship with the sealing member permitting the flow of fluid between the fluid inlet and the fluid outlet. The ball or sphere may be a metallic ball, such as a ball bearing, of stainless steel for example if the valve is to be used in surgical equipment, and the sealing member may be an "O-ring" of a suitable elastomeric or polymeric material. The housing is preferably formed of a polymeric material, for example Delrin, a trademarked product of the General Electric Company, Schenectady, New York, U.S.A. It is preferable that the source of magnetic force be positioned external to the housing, and may be a relatively small permanent magnet positioned adjacent the housing and controlled by a solenoid and switch arrangement.

In accordance with the present invention, a modular control valve apparatus is provided having at least one, and preferably a plurality, of valves as described above. The modular control valve apparatus having a plurality of valves, hereinafter called a module, includes a housing as described in the preceding paragraph, but having a plurality of valve cavities in the housing, each having a fluid inlet and a fluid outlet, and a passage from a source of fluid or aspiration to an instrument or other device to direct and/or utilize the fluid or aspiration. Where the module is used with or as part of ultrasonic surgical apparatus, the instrument to which the fluid or aspiration from the module is connected can be a handpiece, as described in U.S. Pat. Nos. 4,180,074 and 4,184,510.

The module of the present invention may desirably be made of two or more housing sections, by having suitable borings in the sections to form the valve cavities, the fluid passageways, and provisions for fittings for conduits, such as tubing, to transmit fluid and/or aspiration to the module and from the module to the instrument or other device. The fittings desirably can be Luer taper plastic fittings, or other fittings, which can be press or friction fit into suitable borings in the housing, which borings are in fluid communication with the corresponding passageways within the housing. The module can be readily assembled by forming the valve cavities at the ends of the sections where the sections are to be joined or abutted, and similarly having passageways extend from one section to the other where necessary, where the sections are to be joined or abutted. The sections can be secured together by adhesive or other means, but preferably the sections are secured to each other by a frame or clamp member extending along one dimension of the housing, for example the back of the housing, and extending and holding the top and bottom of the housing, while the source of magnetic force may be positioned at the front of the housing.

As heretofore noted, it is often critical to the success of a surgical procedure to precisely control the pressure in an organ or a closed body cavity, such as the human or animal eye. U.S. Pat. No. 4,180,074 discusses the difficulty encountered in attempting to control the pressure in the body cavity, and suggests a system of having a parallel chamber for such purpose. In an embodiment of the present invention precise pressure measurement and control is provided by including one or more pressure monitors, in large part within the housing of the module, coupled to the passageways leading to the fluid flow conduits, e.g., connected to the irrigation and/or aspiration conduits. For example, one or more diaphragms can be included in the housing, conveniently positioned in recesses in a surface of the housing, coupled to passageways connected to the aforementioned conduits, with variations in pressure in the conduits being transmitted from the diaphragm to a sensor, such as a transducer as known to the art, external to the housing to generate a signal, which activates a correcting electronic circuit which in turn controls a pump for a vacuum system. Provision is made to prevent contamination of the monitoring system by providing a hydrophobic filter between each passageway leading to the conduit and the diaphragm, and providing sealing "O-rings" where the passageway between the hydrophobic filter and the connection with the sensor is divided by the junction of two sections of the housing.

The present invention will be more fully understood from the accompanying drawings which are to be read in conjunction with the description of the preferred embodiment, both showing and describing for illustration, a control and monitoring module for use with an ultrasonic surgical instrument, such as a phacoemulsifier. However, it should be understood that this invention is applicable to a single control valve in a housing having a fluid inlet and a fluid outlet as described herein or to a monitoring system as heretofore explained.

DESCRIPTION OF THE PREFERRED EMBODIMENTS

Figure 1:
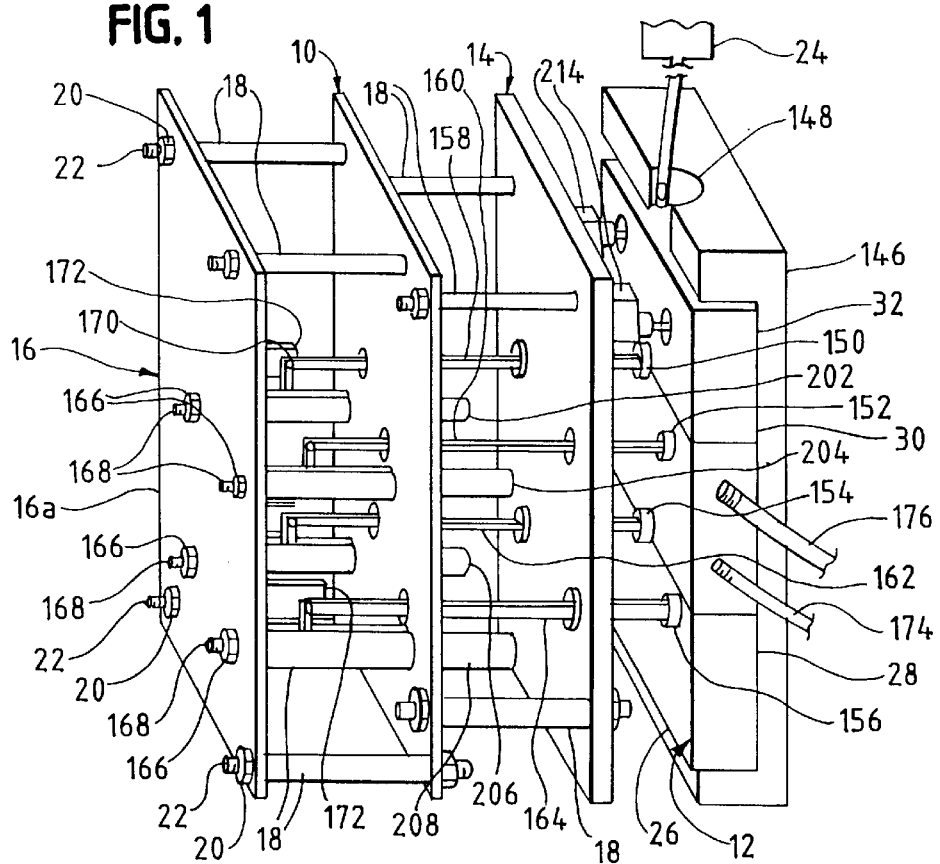
FIG. 1 is a front perspective view of a control and monitoring module in accordance with the present invention, with electronic components omitted for clarity.
Figure 2:
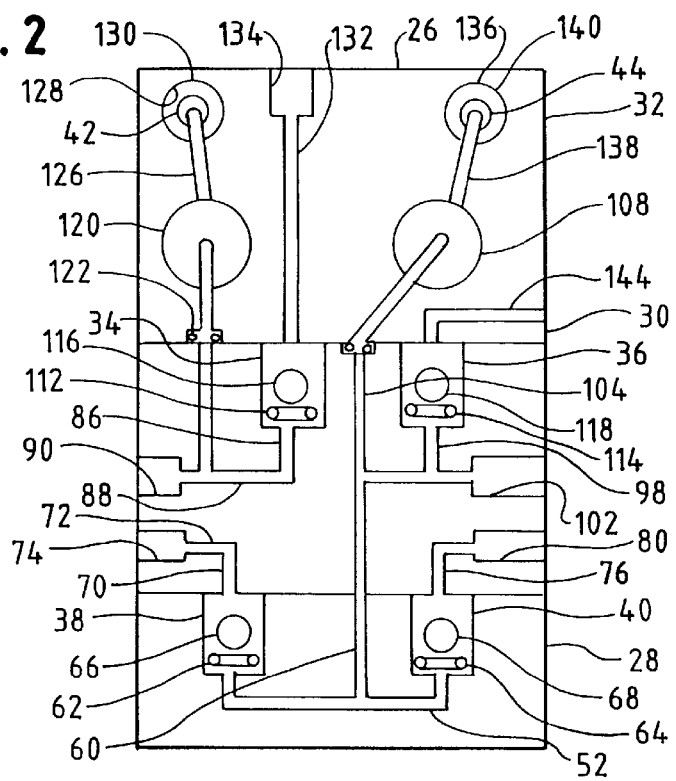
FIG. 2 is a schematic drawing of the housing of the module of FIG. 1 showing a plurality of valves, a plurality of monitoring devices, and passageways and inlet and outlet ports.

In the preferred embodiment of the present invention as illustrated in the drawing, the reference numeral 10 generally shows a control valve and monitoring module in accordance with the present invention. Module 10 includes a valve unit 12, a printed circuit board 14 (components are omitted for clarity), and a valve actuating unit 16. The units 12, 14 and 16 are held in position by spacers 18 which are fastened to the units by nuts 20 threaded on studs 22 passing through spacers 18. External to module 10 is a bag 24 of irrigating liquid which is suspended above module 10 so the irrigating liquid will flow by gravity to the module, a peristaltic pump (not shown), which may be the pump shown in U.S. Pat. No. 4,189,286, or an improvement thereon as commercially sold with phacoemulsifiers, to provide vacuum for aspiration as will be hereinafter described, and a pair of handpieces (not shown) of the type known to the art for performing phacoemulsification.

Figure 3:
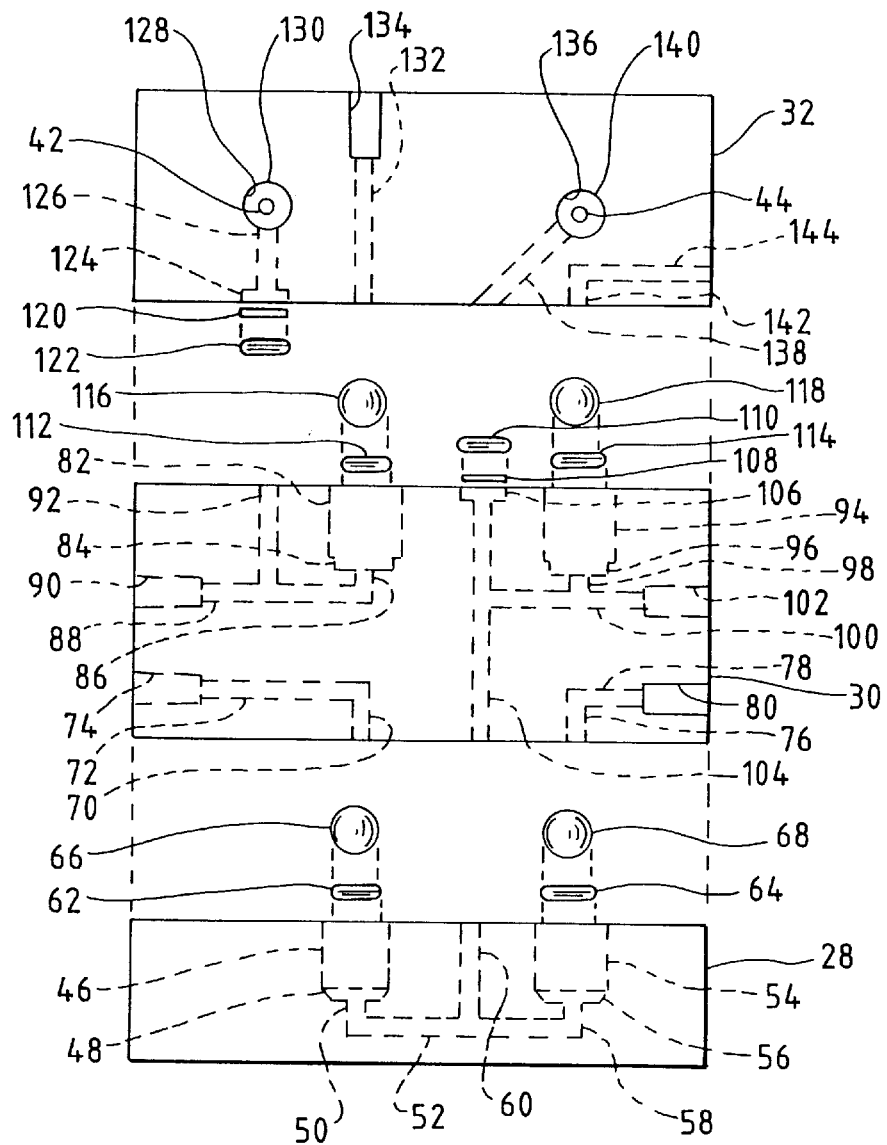
FIG. 3 is an exploded front view of the housing, valves and monitoring device components shown in FIGS. 1 and 2.

Valve unit 12 includes a housing 26 of polymeric material, and in the illustrated embodiment consists of three sections, a bottom section 28, a middle section 30, and a top section 32. Housing 26 includes four valves, 34, 36, 38 and 40, and two pressure sensing ports 42 and 44. As best shown in FIG. 3, bottom section 28 includes a valve cavity 46 for valve 38 which in this embodiment is an aspiration check valve for controlling the aspiration applied to a phacoemulsifier handpiece, for brevity sometimes referred to herein as a Phaco valve 38, the system utilizing the same as the "Phaco system", and components utilized in connection therewith also referred to using the term "Phaco". Cavity 46 has a bottom portion 48 of lesser diameter than the diameter of the remainder of cavity 46. Cavity 46 is in communication with a passageway 50. Cavity 46, portion 48 and passageway 50 are readily formed in bottom section 28 by drilling successively narrower holes from the top of the section along the same center line. Passageway 50 is connected to a horizontal passageway 52 which can be formed by drilling a hole from the right side of section 28 (as viewed in FIG. 3), and then plugging the opening at the right side. A second valve cavity 54 for valve 40 is formed in section 28. Valve 40 in this embodiment serves as a check valve for aspiration applied to a vitrectomy handpiece, and is sometimes referred to herein as a vitrectomy valve. Cavity 54 has a bottom portion 56 of lesser diameter than the diameter of cavity 54 and communicates with a passageway 58, all of which can be formed in the same manner as cavity 46, portion 48 and passageway 50. Passageway 58 intersects and is in communication with passageway 52. A passageway 60 extends downwardly from the top of bottom section 28 and intersects and is in communication with horizontal passageway 52. Passageway 60 is readily formed by drilling from the top of section 28 until the drill passes through passageway 52.

The valves 38 and 40 in the bottom section 28 can be assembled by placing "O-rings" 62 and 64 in the bottom portions 48 and 56 of cavities 46 and 54, respectively, and placing over the "O-rings" 62 and 64 in cavities 46 and 54, stainless steel ball bearings 66 and 68, respectively.

Next, as shown in FIG. 3, middle section 30 of housing 26 can be placed on top of section 28. Middle section 30 includes a passageway 70, which can be drilled from the bottom of section 30, which is in communication with cavity 46 upon section 30 being placed on section 28. Another passageway 72, which can be drilled from the left side of section 30, intersects and is in communication with passageway 70, and ends in an enlarged opening 74 in the left side of section 30 by drilling therein, into which a Luer taper plastic fitting (not shown) can be friction fit. Similarly, middle section 30 includes a passageway 76 intersecting and in communication with cavity 54 upon section 30 being placed on section 28, which intersects and is in communication with a passageway 78 and an enlarged opening 80 to receive a fitting as in the case of opening 74, drilled into the right side of section 30.

Middle section 30 also includes a cavity 82 for a valve 34, which in this embodiment controls the flow of irrigation liquid, and hence may be referred to as irrigation valve 34. Cavity 82 has a bottom portion 84 of lesser diameter than the diameter of cavity 82 and a passageway 86 extending beneath portion 84, all of which can be formed by drilling from the top of section 30 along the same center line. Another passageway 88, which can be drilled from the left side of section 30, intersects and is in communication with passageway 86, and ends in an enlarged opening 90 in the left side of section 30 by drilling therein, into which a Luer taper plastic fitting (not shown) can be friction fit. A passageway 92 extends downwardly from the top of middle section 30 and intersects and is in communication with horizontal passageway 88. Passageway 92 is readily formed by drilling from the top of section 30 until the drill passes through passageway 88.

Middle section 30 includes still another cavity 94 for valve 36, in this embodiment a vent valve for venting aspiration vacuum. Cavity 94 has a bottom portion 96 of lesser diameter than the diameter of cavity 94 and a passageway 98 extending beneath portion 96, all of which can be formed by drilling from the top of section 30 along the same center line. Another passageway 100, which can be drilled from the right side of section 30, intersects and is in communication with passageway 98, and ends in an enlarged opening 102 in the right side of section 30 by drilling therein, into which a Luer taper plastic fitting (not shown) can be friction fit. A passageway 104 extends downwardly from the top and through middle section 30 and intersects and is in communication with horizontal passageway 100. Passageway 104 is readily formed by drilling from the top through section 30 and intersecting passageway 100. The top of passageway 104 at the top surface of section 30 has a recess 106 adapted to receive a disk 108 of hydrophobic filter paper, which will prevent water, aqueous solutions, suspensions and mixtures, and moisture from passing therethrough, and also an "O-ring" 110 to seal passageway 104 from leakage upon top section 32 being placed on middle section 30.

The valves 34 and 36 in the middle section 30 can be assembled by placing "O-rings" 112 and 114 in the bottom portions 84 and 96 of cavities 82 and 94, respectively, and placing over the "O-rings" 112 and 114 in cavities 82 and 94, stainless steel ball bearings 116 and 118, respectively.

Prior to placing top section 32 on middle section 30, a disk 120 of hydrophobic filter paper identical to or substantially similar to disk 108 and an "O-ring" 122 is placed on top of the end of passageway 92 to fit within a recess 124 formed in the bottom of section 32 aligned with passageway 92. Top section 32 includes a passageway 126 leading from recess 124 to pressure sensing port 42, which is formed by a recess 128 in the front surface of section 32 in communication with passageway 126 and an O-ring 130 positioned in recess 128. Top section 32 also includes a passageway 132 extending from the top to the bottom of the section, and terminating at its upper end in an enlarged opening 134 into which a Luer taper plastic fitting (not shown) can be friction fit. Top section 32 further includes a second pressure sensing port 44, which is formed by a recess 136 in the front surface of section 32 which is in communication with a passageway 138 which extends to the bottom edge of section 32 and is placed in sealed communication with passageway 104 when top section 32 is placed on middle section 30. Passageway 138 can be formed in section 32 by drilling from the bottom of the section at an angle. An "O-ring" 140 is positioned in recess 136 for the purpose of sealing the port. Another passageway 142 is formed in section 32 by drilling from the bottom of the section aligned with valve cavity 94, and intersects and communicates with a passageway 144 serving as a vent as will be hereinafter described.

Referring to FIG. 1, sections 28, 30 and 32 of housing 26 are secured in position by a clamping member 146, which, as shown, can be a stainless steel U-shaped bracket into which the assemble housing 26 can be placed. The top of bracket 146 has a recess 148 to provide clearance for tubing extending from a fitting in enlarged opening 134 in housing 26 to irrigation bag 24 suspended above module 10 to allow irrigation liquid to flow by gravity into passage 132 of the module. Valves 34, 36, 38 and 40 are controlled by magnets 150, 152, 154 and 156 which are secured to the ends of actuating arms 158, 160, 162 and 164, respectively, and are supported against the front of housing 26 so that magnetic force from each magnet will cause the ball bearing in the respective valve cavity to lift off or seal onto the "O-ring" seat in the bottom portion of the cavity upon activation of solenoids 202, 204, 206 and 208, as will be hereinafter described. The solenoids are secured to the support plate 16a of the valve actuating unit 16 by means of nuts 166 threaded onto studs 168 extending from the solenoid housings and through the plate 16a. Actuating arms 158, 160, 162 and 164 are L-shaped and act as crank arms by pivoting at their crank elbows on fasteners 170 which are pivotally secured to blocks 172 mounted on plate 16a. The ends opposite of the actuating arms opposite the ends secured to the magnets are secured to the solenoid pistons or movable cores to move the magnets upon being pivoted at the crank elbow by the action of the solenoids.

Referring further to FIG. 1, module 10 includes two pressure sensing elements 214, which will hereinafter be described, which are mounted on printed by suitable fasteners (not shown) as known to the art, on printed circuit board 14. Pressure sensing elements 214 include probes 214a which extend toward and whose hollow tips are in sealed engagement with "O-rings" 130 and 140 so as to transmit air pressure or vacuum from ports 42 and 44 to the sensing elements 214. Suitable polymeric tubing used for surgical equipment are connected to fittings secured to enlarged openings 74, 80, 90 and 102, tubing 174 and 176 being shown, and lead there-from to corresponding connections on the handpieces (not shown) to provide controlled irrigation and/or aspiration as described herein.

In the embodiment shown herein, fluid pressure at a surgical site is maintained at an appropriate level by balancing flows of fluids to and from the site. As fluid is introduced to the site through irrigation valve 34, a corresponding amount of fluid is removed through the Phaco valve 38. When the vitrectomy handpiece is in use, irrigation is not employed, and the desired amount of fluid is removed from the surgical site through vitrectomy valve 40. Flow is balanced by control signals derived from pressure sensing ports 42, 44.

Figure 4:
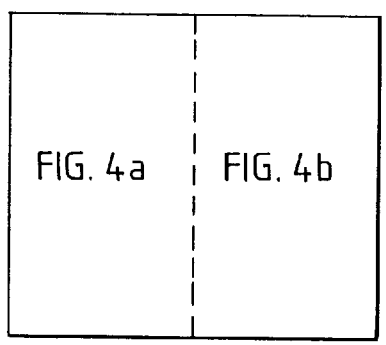
FIG. 4 is a schematic diagram of an electrical control system in accordance with the present invention.
Figure 4A:
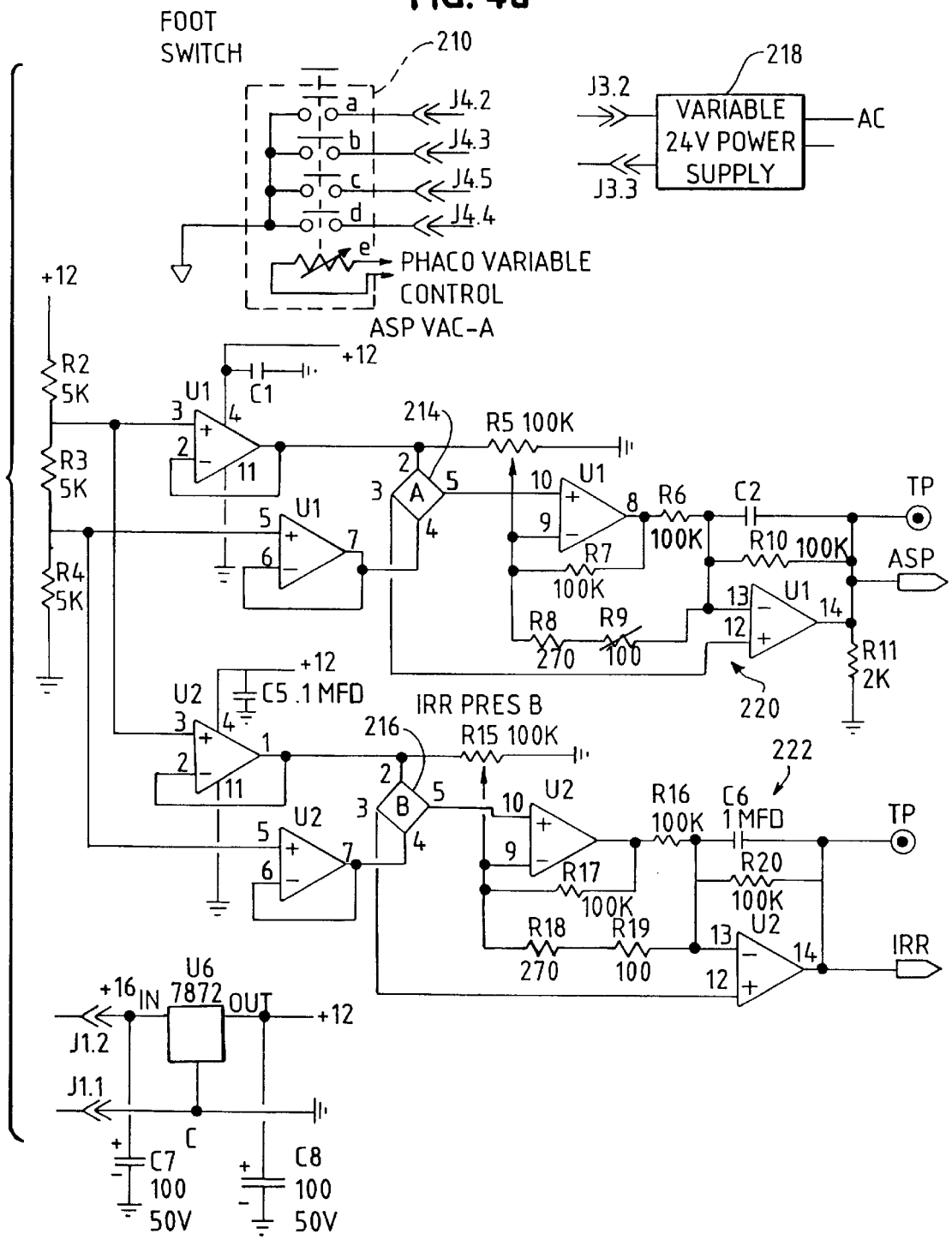
Figure 4B:
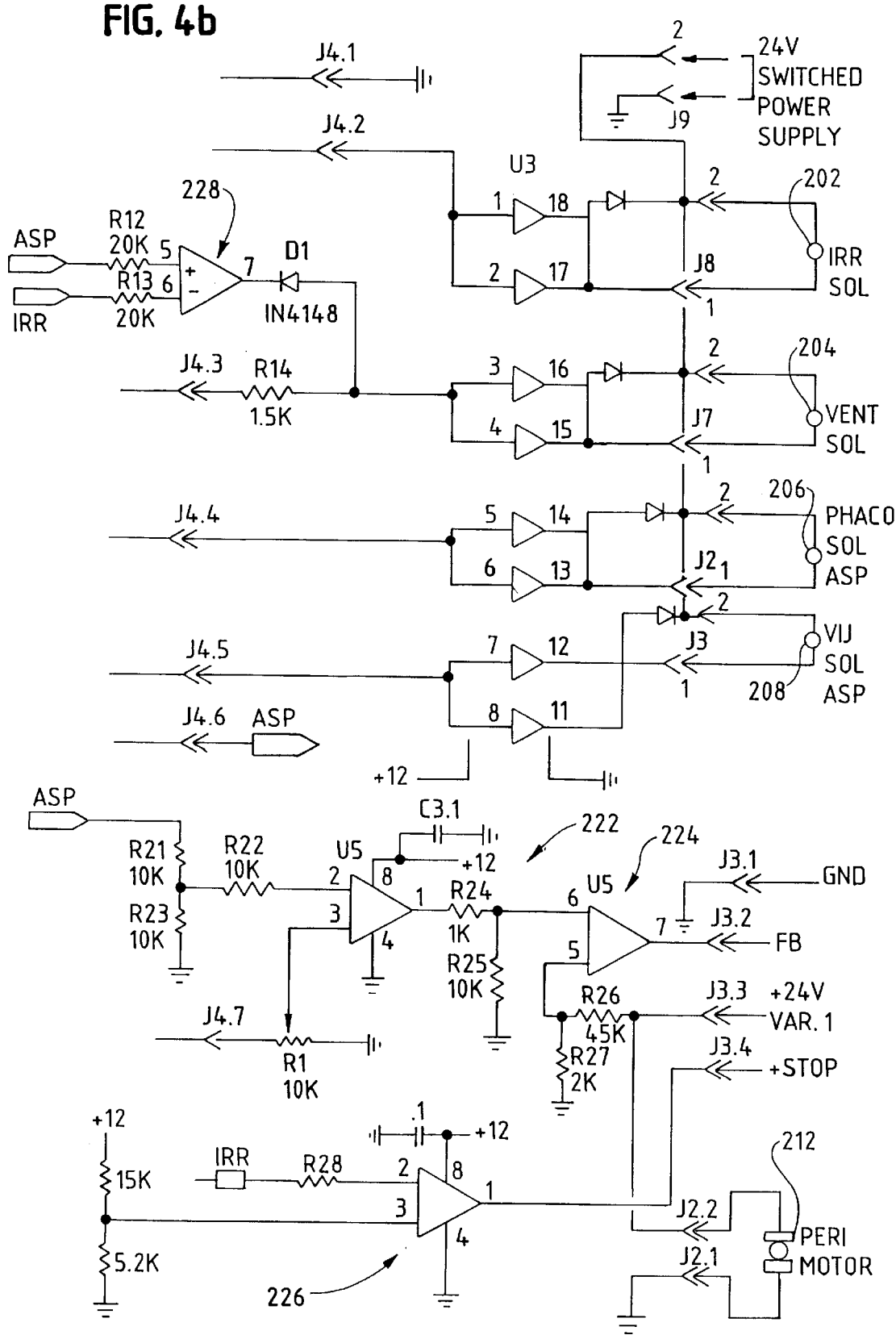

FIG. 4 is a schematic diagram of an electrical control system used to balance fluid flow through the site. As shown, a first solenoid 202 controls the irrigation valve 34. Similarly, a second, third, and fourth solenoid 204, 206, 208 control the vent valve 36, Phaco valve 38 and vitrectomy valve 40, respectively.

The irrigation valve solenoid 202, vent valve solenoid 204, Phaco valve solenoid 206 and vitrectomy valve solenoid 208 are controlled primarily by a foot switch 210. Foot switch 210 may be any sequenced-contact foot switch capable of accepting four normally-open contacts a–d and a variable resistor e. In a deactivated state, the contacts a–d of foot switch 210 are open and the variable resistor e presents a maximum resistance to the Phaco system. As the foot switch 210 is depressed to a first detent position, the first contact a closes, activating the irrigation valve solenoid 202. As the foot switch 210 is depressed to a second detent position, contacts a–d close activating the solenoid valves 202, 204, 206, 208, depending on the controls selected in accordance with the handpiece and the procedure being utilized.

As the foot switch 210 is moved to the first and second detent positions the variable resistor e remains at a maximum resistance level providing a minimum speed output signal to the Phaco variable control system. As the foot switch 210 is moved past the second detent position, the variable resistance e decreases, provides a progressively higher signal level to the Phaco control system.

Under the embodiment, fluid flow through the valves 34, 36, 38, 40 is accomplished by the combination of gravity from a irrigation fluid source (bag of irrigating fluid 24) and by operation of a peristaltic pump providing vacuum for aspiration driven by a peristaltic motor 212. Where a surgeon determines that irrigating fluid of a higher pressure is required, the bag 24 is raised in elevation to a higher level. Where less irrigating fluid is required the bag is lowered. The peristaltic pump motor 212 is operated at a variable speed to accommodate the varying fluid flows from the fluid source.

The speed of the peristaltic pump motor 212 is based upon a pressure signal detected at a pressure sensing port 44. Where more irrigating fluid is delivered from the bag 24 (due to the bag 24 being placed at a higher elevation), the peristaltic pump motor 212 must be operated at a higher speed to remove the irrigating fluid. Where less irrigating fluid is delivered, the peristaltic motor 212 may be operated at a lower speed.

Pressure sensing for control of the peristaltic pump motor 212 may be accomplished by any low pressure electromechanical sensing element (e.g., a Sensyn Model No. SCX30DNC) 214. Under the embodiment, the pressure sensing element 214 of FIG. 4 is connected to a differential amplification circuit 220 to provide an aspiration pressure reference signal. The pressure reference signal is scaled in scaling amplifier 220 before being applied to a feedback amplifier 224, coupled to a variable power supply 218. The output of the variable power supply 218 serves the dual purpose of driving the peristaltic motor pump 212 as well as providing a feedback signal to the amplifier 224.

Also provided for pressure control is an irrigation pressure sensor 216 interconnected with a pressure sensing port 42 of the irrigation fluid supply. The irrigation pressure sensor 216 is used with a differential amplification circuit 222 to provide a pressure reference signal for the irrigation fluid source. The pressure reference signal from the irrigation fluid source is scaled in a scaling amplifier 226 and provided as a safety signal through plug reference J3.4 to interrupt system operation in the event of an overpressure in the irrigation fluid system.

The pressure reference signals from both the irrigation sensor 216 and aspiration sensor 214 are also applied to a vent control amplifier 228. Vent control amplifier 228 is used primarily to vent the vacuum from the peristaltic pump during periods of inactivity between activation of foot switch 210.

We claim:

1. Apparatus for controlling aspiration through a surgical handpiece operating at a surgical site during surgery, such apparatus comprising:
   a pressure sensor coupled to an outlet of the handpiece for determining an aspiration pressure value at an aspirator outlet of the surgical handpiece operating at the surgical site;
   a variable speed aspirator coupled to the outlet of the handpiece for aspirating fluid from the surgical handpiece at a flow rate based upon the determined pressure value at the aspirator outlet;
   a foot operated switch coupled to the aspirator for activating the aspirator;
   means coupled to the outlet of the handpiece for venting the aspirator outlet of the handpiece upon deactivation of the footswitch.

2. The apparatus as in claim 1 wherein the variable aspirator further comprises a peristaltic pump.

3. The apparatus as in claim 1 further comprising a motor speed controller operably connected to the pressure sensor.

4. The apparatus as in claim 1 further comprising a foot switch for providing a motor speed control signal to the motor speed controller.

5. The apparatus as in claim 1 further comprising an irrigation source supplying an irrigant to the surgical site through the handpiece.

6. The apparatus as in claim 1 further comprising a solenoid valve for controlling the flow of irrigant to the handpiece.

7. The apparatus as in claim 1 further comprising a solenoid valve for controlling flow of the aspirated fluid.

8. Apparatus for controlling irrigation and aspiration at a surgical site during surgery, such apparatus comprising:
   a surgical handpiece;
   a irrigation source connected to the handpiece via an irrigation passageway and supplying an irrigant to the surgical site through the irrigation passageway and handpiece;
   means disposed within the irrigation passageway for blocking the irrigation passageway;
   a pressure sensor coupled to an aspirator outlet of the surgical handpiece for determining an aspiration pressure value in an aspirator passageway the aspirator outlet of the surgical handpiece operating at the surgical site;
   a variable speed aspirator coupled to the aspirator outlet for aspirating fluid from the surgical handpiece at a flow rate based upon the determined pressure value at the aspirator outlet;
   means for blocking the aspirator passageway between the handpiece and the variable speed aspirator disposed in the aspirator passageway between the handpiece and variable speed aspirator;
   means for venting the aspirator passageway coupled to the aspirator passageway between the means for blocking the aspirator passageway and handpiece; and
   a footswitch coupled to the means for blocking and means for venting for unblocking the means for blocking the irrigator passageway and aspirator passageway and for closing the means for venting.

9. The apparatus as in claim 8 wherein the variable aspirator further comprises a variable speed motor.

10. The apparatus as in claim 8 wherein the variable aspirator further comprises a peristaltic pump.

11. The apparatus as in claim 8 further comprising a motor speed controller operably connected to the pressure sensor.

12. The apparatus as in claim 8 further comprising a foot switch for providing a motor speed control signal to the motor speed controller.

13. The apparatus as in claim 8 further comprising an irrigation source supplying an irrigant to the surgical site through the handpiece.

14. The apparatus as in claim 8 further comprising a solenoid valve for controlling the flow of irrigant to the handpiece.

15. The apparatus as in claim 8 further comprising a solenoid valve for controlling flow of the aspirated fluid.

16. Apparatus for controlling irrigation and aspiration at a surgical site during surgery, such apparatus comprising:
- a surgical handpiece operating at the surgical site;
- a irrigation source operably connected to the handpiece and supplying an irrigant to the surgical site through the surgical handpiece;
- a first solenoid activated valve disposed within a passageway leading from the irrigation source to the handpiece for controlling flow of irrigant from the irrigation source to the surgical site through the surgical handpiece;
- a pressure sensor coupled to a passageway leading from an aspirator outlet of the surgical handpiece for determining an aspiration pressure value at the aspirator outlet of the surgical handpiece;
- a variable aspirator coupled to the passageway leading from the aspirator outlet of the surgical handpiece for aspirating fluid from the surgical handpiece at a flow rate based upon the determined pressure value at the aspirator outlet;
- a second solenoid activated valve disposed in the passageway between the aspirator outlet of the handpiece and the variable aspirator for controlling flow of aspirating fluid from the handpiece to the variable aspirator; and
- a footswitch coupled to the first and second solenoids and variable aspirator for activating the first and second solenoids and variable aspirator.

17. The apparatus as in claim 16 wherein the first solenoid activated valve further comprises a spherical, magnetically permeable first flow control element operating between a first position where the first flow control element blocks flow of the irrigant through the solenoid activated valve and a second position wherein the first flow control element allows flow of irrigant through the solenoid activated valve.

18. The apparatus as in claim 17 further comprising a permanent magnet operating between a first and second position magnetically coupled to the first flow control element and isolated from a flow path of the irrigant for inducing the first flow control element to move between a corresponding position of the first and second position.

19. The apparatus as in claim 16 wherein the second solenoid activated valve further comprises a spherical, magnetically permeable second flow control element operating between a first position where the second flow control element blocks flow of the aspirated fluid through the solenoid activated valve and a second position wherein the second flow control element allows flow of aspirated fluid through the solenoid activated valve.

20. The apparatus as in claim 19 further comprising a permanent magnet operating between a first and second position magnetically coupled to the second flow control element and isolated from a flow path of the aspirated fluid for inducing the second flow control element to move between a corresponding position of the first and second position.

* * * * *

UNITED STATES PATENT AND TRADEMARK OFFICE
CERTIFICATE OF CORRECTION

PATENT NO. : 5,904,669
DATED : May 18, 1999
INVENTOR(S) : Schildgen et al.

It is certified that error appears in the above-identified patent and that said Letters Patent is hereby corrected as shown below:

In the Claims:

Col. 8, line 33, delete the words "in an aspirator passageway", and substitute therefor --at--.

Signed and Sealed this

Ninth Day of November, 1999

Attest:

Q. TODD DICKINSON

Attesting Officer

Acting Commissioner of Patents and Trademarks